(12) United States Patent
Price et al.

(10) Patent No.: US 10,149,815 B2
(45) Date of Patent: Dec. 11, 2018

(54) TOOTHPASTE AND MOUTH RINSE

(71) Applicant: EWC & Associates, LLC, Phoenix, AZ (US)

(72) Inventors: Ginger Price, Phoenix, AZ (US); Martin Giniger, New York, NY (US)

(73) Assignee: EWC & Associates, LLC, Phoenix, AZ (US)

( * ) Notice: Subject to any disclaimer, the term of this patent is extended or adjusted under 35 U.S.C. 154(b) by 86 days.

(21) Appl. No.: 15/207,406

(22) Filed: Jul. 11, 2016

(65) Prior Publication Data
US 2017/0007533 A1    Jan. 12, 2017

Related U.S. Application Data

(60) Provisional application No. 62/190,298, filed on Jul. 9, 2015.

(51) Int. Cl.
| | | |
|---|---|---|
| *A61K 8/25* | (2006.01) | |
| *A61K 8/92* | (2006.01) | |
| *A61Q 11/00* | (2006.01) | |
| *A61K 8/42* | (2006.01) | |
| *A61K 8/27* | (2006.01) | |
| *A61K 8/34* | (2006.01) | |
| *A61K 8/60* | (2006.01) | |
| *A61K 8/368* | (2006.01) | |
| *A61K 8/29* | (2006.01) | |
| *A61K 8/46* | (2006.01) | |

(52) U.S. Cl.
CPC ............... *A61K 8/922* (2013.01); *A61K 8/25* (2013.01); *A61K 8/27* (2013.01); *A61K 8/29* (2013.01); *A61K 8/345* (2013.01); *A61K 8/368* (2013.01); *A61K 8/42* (2013.01); *A61K 8/463* (2013.01); *A61K 8/60* (2013.01); *A61Q 11/00* (2013.01); *A61K 2800/30* (2013.01)

(58) Field of Classification Search
USPC .......................................................... 424/49
See application file for complete search history.

(56) References Cited

U.S. PATENT DOCUMENTS

| | | | | |
|---|---|---|---|---|
| 5,906,811 | A * | 5/1999 | Hersh ...................... | A61K 8/02 424/49 |
| 9,044,466 | B2 * | 6/2015 | Cohen .................. | A61K 31/435 |
| 9,114,097 | B1 * | 8/2015 | Aminpour ................ | A61K 8/97 |
| 2012/0244087 | A1 * | 9/2012 | Trivedi .................. | A23G 4/068 424/48 |
| 2015/0147368 | A1 * | 5/2015 | Goode ..................... | A61K 8/25 424/401 |

* cited by examiner

*Primary Examiner* — Nannette Holloman
(74) *Attorney, Agent, or Firm* — David G. Rosenbaum; J. Peter Paredes; Rosenbaum IP, P.C.

(57) ABSTRACT

Formulations for oral care products that incorporate coconut oil for effectively removing bacteria from the mouth and methods for making these products are disclosed herein. A preferred mouth rinse contains alkaline water, coconut flavor oil extract, sodium lauryl sarcosinate, zinc chloride, 30% xylitol solution, glycerin, aloe barbadensis leaf juice, and optionally, sodium benzoate, de-ionized water, and mint flavor extract. A preferred toothpaste contains alkaline water, coconut oil, hydrated sylica sident 9, hydrated silica sident 22s, glycerin, xylitol, Irish moss, sodium coco sulphate, aloe babadensis leaf juice, titanium dioxide, and flavor. The percentage of the coconut oil content in the preferred products is in the range of 20%-80%, but most preferably 40%-60%.

10 Claims, 2 Drawing Sheets

FIG. 1:

Holistic and Healthy Coconut Alcohol Free Mouth Rinse

|  | % |
|---|---|
| Phase A | |
| Alkaline Water | 40.375 |
| Pure Coconut Flavor Oil Extract | 12.626 |
| Phase B | |
| Alkaline Water | 12.178 |
| Sodium Lauryl Sarcosinate | 0.022 |
| Phase C | |
| Zinc Chloride | 0.7 |
| 30% Xylitol Solution | 10 |
| Phase D | |
| Glycerin | 10 |
| Aloe Barbadensis Leaf Juice | 4 |
| Phase E | |
| Sodium Benzoate | 0.099 |
| Phase F | |
| De-ionized Water | 9.7 |
| Natural Mint Flavor Extract | 0.3 |

FIG. 2:

Holistic and Healthy Coconut Oil Toothpaste

| FORMULA | % |
|---|---|
| Alkaline Water | 35.5 |
| Coconut Oil | 27.75 |
| Hydrated Sylica Sident 9 | 15.4 |
| Hydrated Silica Sident 22s | 2.8 |
| Glycerin | 10.5 |
| Xylitol | 4 |
| Irish Moss | 1.4 |
| Sodium Coco Sulphate | 0.7 |
| Organic Aloe Barbadensis Leaf Juio | 0.7 |
| Titanium Dioxide | 0.65 |
| Flavor | 0.6 |

TOOTHPASTE AND MOUTH RINSE

BACKGROUND

Oral inflammation and the bacteria that causes it are the enemy of good and stable oral health. Preventing oral inflammation saves a person from not only pain and discomfort but also expense and trouble of doctor visits and treatments. Coconut oil has been used in oral health practices to aid in removal of bacteria from the mouth. The use of coconut oil has been proven effective in this line of use, and therefore, has been incorporated into oral health practices. In addition, the use of coconut oil helps people maintain good oral and dental health without using fluoride.

It is thus desirous to have oral care products that uses coconut oil in order to effectively remove the bacterial that causes oral inflammation.

SUMMARY

The structure, overall operation and technical characteristics of the present invention will become apparent with the detailed description of preferred embodiments and the illustration of the related drawings as follows.

This invention is embodied in formulations for oral care products including a toothpaste and a mouth rinse that incorporate coconut oil and its helpful properties and methods for making such products. The high content of coconut oil in these products distinguishes them from the prior art and accentuates the useful properties of the products.

One object of this invention is to provide formulations for oral care products that accentuate the useful properties of coconut oil in removing the bacteria that cause oral inflammation.

Another object of this invention is to provide methods for making such oral care products.

BRIEF DESCRIPTION OF THE FIGURES

FIG. 1 is a table showing a preferred formulation of a mouth rinse having coconut oil.

FIG. 2 is a table showing a preferred formulation of a toothpaste having coconut oil.

DESCRIPTION OF THE EMBODIMENTS

FIG. 1 shows the details of a preferred formulation of the coconut alcohol free mouth rinse. The preferred mouth rinse is prepared in 6 separate phases and then all 6 phases are mixed together in order. Phase A contains 40.375% Alkaline Water and 12.626% Pure Coconut Flavor Oil Extract. Phase B contains 12.178% Alkaline Water and 0.022% Sodium Lauryl Sarcosinate. Phase C contains 0.7% Zinc Chloride and 10% 30% Xylitol Solution. Phase D contains 10% Glycerin and 4% Aloe Barbadensis Leaf Juice. Phase E contains 0.099% of Sodium Benzoate. Phase F contains 9.7% De-ionized Water and 0.3% Natural Mint Flavor Extract.

While this is the preferred embodiment of the mouth rinse mixture, the percentages of ingredients can be varied. In particular, the coconut oil content of the mixture is in the range of 20%-80%, but most preferably 40%-60%. Phases E and F may be omitted.

The preferred instructions for mixing the mouth rinse comprise first, pre-mixing a 30% Xylitol Solution. Second, Phase A, Phase B, Phase C, Phase D, and Phase F are each mixed separately. They are mixed until the solution is clear. Finally, Phases A, B, C, D, E, and F are combined in order. Mix at slow speed until homogeneous. The Xylitol solution, mint flavor, and coconut flavor can be adjusted to taste.

FIG. 2 shows the details of a preferred formulation of the coconut oil toothpaste. The toothpaste contains 35.5% Alkaline Water, 27.75% Coconut Oil, 15.4% Hydrated Sylica Sident 9, 2.8% Hydrated Silica Sident 22s, 10.5% Glycerin, 4% Xylitol, 1.4% Irish Moss, 0.7% Sodium Coco Sulphate, 0.7% Organic Aloe Barbadensis Leaf Juice, 0.65% Titanium Dioxide, and 0.6% Flavor.

While this is the preferred embodiment of the toothpaste mixture, the percentages of ingredients can be varied. In particular, the coconut oil content of the mixture is in the range of 20%-80%, but most preferably 40%-60%.

The preferred instructions for mixing the toothpaste comprise, first, to a clean sanitized vessel with sweep agitation and homogenization add Water, Sodium Coco Sulphate, Xylitol, Glycerin and Titanium Dioxide. Second, mix 5 minutes between ingredient additions under sweeps (16±2 RPM). Third, once all ingredients have been added at 16±2 RPM, continue mixing for 30 minutes under vacuum.

Next, in a separate vessel blend the Irish Moss and Silica. Use ⅓ of Sident 9 and ⅓ of Irish Moss and mix by hand. Repeat 2 more times in the same container, until all Sident 9 and Irish Moss are mixed. Add this first ⅓ of the pre-mix to the main vessel with homogenizer ON under vacuum at 16±2 RPM. Repeat 2 more times until all of the pre-mix has been added. Mix for 10 more minutes. Add Sident 22s to the main vessel and continue mixing under vacuum.

Once the main vessel is uniformly mixed, add the Aloe Juice and the Flavor. Continue to mix (16±2 RPM) under vacuum with sweeps for 30 minutes. Once everything is homogenous and looking like finished toothpaste, add Coconut Oil at 16±2 RPM with NO Homogenizer under vacuum. QC to analyze and taste. Package to portable container for filling.

Additionally, a preferred embodiment of the toothpaste with at least 40% of natural coconut oil is shown to have a strong antimicrobial effect, as well as satisfactory whitening and breath freshening effects. A clinical study of this preferred embodiment shows that the embodiment killed 99% of all microorganisms tested. In contrast, the placebo and the control toothpaste (the Crest™ anti-cavity toothpaste) did not show antimicrobial activity against any of the 23 tested microorganisms. Furthermore, this embodiment was the only formulation in the study that had activity against Grain-negative bacteria (*Pseudomonas aeruginosa*) which is a critical bacterial species that contributes to periodontal disease. Therefore, the preferred toothpaste can be used to effectively prevent oral inflammation caused by bacteria.

The aforementioned embodiments are preferably used 2 times daily for maximum benefits. For the preferred toothpastes, it is recommended that a user uses them with a soft bristle toothbrush and brush at least one minute. For the preferred mouth rinse, it is recommended that a user swishes vigorously 10 ml between teeth for at least one minute and then spits out.

While the invention has been described by means of specific embodiments, numerous modifications and variations could be made thereto by those ordinary skilled in the art without departing from the scope and spirit disclosed herein.

What is claimed is:

1. A mouth rinse comprising:
   a. Alkaline water, wherein a percentage of the alkaline water is between 35.5% and 52.553%;

b. Coconut flavor oil extract, wherein a percentage of the coconut flavor oil extract is between 20%-80%;
c. Sodium lauryl sarcosinate, wherein a percentage of the sodium lauryl sarcosinate is 0.022%;
d. Zinc chloride, wherein a percentage of the zinc chloride is 0.7%;
e. 30% xylitol solution, wherein a percentage of the 30% xylitol solution is 10%;
f. Glycerin, wherein a percentage of the glycerin is 10% or 10.5%; and
g. Aloe barbadensis leaf juice, wherein a percentage of the aloe barbadensis leaf between 0.7% and 4%.

2. The mouth rinse according to claim 1 wherein a percentage of the coconut flavor oil extract is 40%-60%.

3. The mouth rinse according to claim 1 further comprises:
a. Sodium benzoate;
b. De-ionized water; and
c. Mint flavor extract.

4. The mouth rinse according to claim 3 wherein:
a. a percentage of the alkaline water is 52.553%,
b. a percentage of the coconut flavor oil extract is 12.626%,
c. a percentage of the sodium lauryl sarcosinate is 0.022%,
d. a percentage of the zinc chloride is 0.7%,
e. a percentage of the 30% xylitol solution is 10%,
f. a percentage of the glycerin is 10%,
g. a percentage of the aloe barbadensis leaf juice is 4%,
h. a percentage of the sodium benzonate is 0.099%,
i. a percentage of the de-ionized water is 9.7%, and
j. a percentage of the mint flavor extract is 0.3%.

5. A method for creating a mouth rinse comprising the steps of:
a. Mixing a 30% xylitol solution, wherein a percentage of the 30% xylitol solution is 10%;
b. Mixing alkaline water and pure coconut flavor oil extract into Phase A, wherein a percentage of the alkaline water is between 40.375 and a percentage of the coconut flavor oil extract is between 12.626;
c. Mixing alkaline water and sodium lauryl sarcosinate into Phase B, wherein a percentage of the sodium lauryl sarcosinate is 0.022%;
d. Mixing zinc chloride and the 30% xylitol solution into Phase C, wherein a percentage of the 30% xylitol solution is 10% and a percentage of the zinc chloride is between 0.7%;
e. Mixing glycerin and aloe barbadensis leaf juice into Phase D, wherein a percentage of the glycerin is 10% and a percentage of the aloe barbadensis leaf juice is 4%; and
f. Combining Phases A, B, C, D, and flavoring in order and mixing until homogeneous.

6. The method of claim 5 wherein:
a. the flavoring further comprises de-ionized water and mint flavor extract,
b. a percentage of the de-ionized water is 9.7%, and
c. a percentage of the mint flavor extract is 0.3%.

7. The method of claim 6 further comprises the step of mixing the mouth rinse with sodium benzoate, wherein a percentage of the sodium benzoate is 0.099%.

8. A toothpaste comprising:
a. Alkaline water at a percentage of 35.5%;
b. Coconut oil at a percentage of 27.75%;
c. Thickening silica at a percentage of 15.4%;
d. Abrasive silica at a percentage of 2.8%;
e. Glycerin at a percentage of 10.5%;
f. Xylitol at a percentage of 4%;
g. Irish moss at a percentage of 1.4%;
h. Sodium coco sulphate at a percentage of 0.7%;
i. Aloe barbadensis leaf juice at a percentage of 0.7%;
j. Titanium dioxide at a percentage of 0.65; and
k. Flavor at a percentage of 0.6%.

9. A method for creating a toothpaste comprising the steps of:
a. Cleaning a sanitized vessel with sweep agitation and homogenization;
b. Adding water, sodium coco sulphate, xylitol, glycerin, and titanium dioxide while mixing 5 minutes between ingredient additions under sweeps of 16±2 RPM;
c. Continue mixing for 30 minutes under vacuum;
d. Blending in a separate vessel the Irish Moss and thickening silica wherein ⅓ or the thickening silica and ⅓ of the Irish Moss is added at a time until all is blended;
e. Adding ⅓ of the Irish Moss/thickening silica mixture at a time to the water, sulphate, xylitol, glycerin, titanium dioxide mixture in the main vessel with the homogenizer on under vacuum at 16±2 RPM until all of the mix has been added and continue mixing for 10 minutes;
f. Adding abrasive silica to the sanitized vessel and continue mixing under vacuum;
g. Adding aloe juice and flavor and mixing until homogenous;
h. Mixing 16±2 RPM under vacuum with sweeps for 30 minutes until completely homogenous; and
i. Adding coconut oil at 16±2 RPM with homogenizer under vacuum.

10. The method of claim 9 wherein:
a. a percentage of the alkaline water is 35.5%,
b. a percentage of the coconut oil is 27.75%,
c. a percentage of the thickening silica is 15.4%,
d. a percentage of the abrasive silica is 2.8%,
e. a percentage of the glycerin is 10.5%,
f. a percentage of the xylitol is 4%,
g. a percentage of the Irish Moss is 1.4%,
h. a percentage of the sodium coco sulphate is 0.7%,
i. a percentage of the aloe barbadensis leaf juice is 0.7%,
j. a percentage of the titanium dioxide is 0.65%, and
k. a percentage of the flavor is 0.6%.

* * * * *